(12) United States Patent
Feldhues et al.

(10) Patent No.: US 6,248,887 B1
(45) Date of Patent: Jun. 19, 2001

(54) PROCESS FOR PREPARING BIS-ALKOXY-TRIAZINYL-AMINO-CONTAINING STILBENE DISULPHONIC ACIDS OR THEIR DERIVATIVES

(75) Inventors: Ulrich Feldhues, Charleston, SC (US); Uwe Vogt, Monheim (DE); Udo Eckstein, Köln (DE); Rolf Brockmann; Dietmar Fiedel, both of Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/077,120

(22) PCT Filed: Nov. 15, 1996

(86) PCT No.: PCT/EP96/05033

§ 371 Date: May 21, 1998

§ 102(e) Date: May 21, 1998

(87) PCT Pub. No.: WO97/19937

PCT Pub. Date: Jun. 5, 1997

(30) Foreign Application Priority Data

Nov. 28, 1995 (DE) ............................................... 195 44 269

(51) Int. Cl.[7] ................................................. C07D 251/68
(52) U.S. Cl. ......................................................... 544/193.2
(58) Field of Search .......................................... 544/193.2

(56) References Cited

U.S. PATENT DOCUMENTS

| 2,713,046 | * | 7/1955 | Williams et al. | 544/193.2 |
| 3,371,089 |   | 2/1968 | Gold et al. | 544/193.2 |
| 3,682,907 |   | 8/1972 | Ohkawa et al. | 544/193.2 |
| 3,951,965 | * | 4/1976 | Mengler et al. | 544/193.2 |
| 4,466,900 |   | 8/1984 | Horlacher et al. | 544/193.2 |
| 4,866,152 | * | 9/1989 | Lo | 544/193.2 |

FOREIGN PATENT DOCUMENTS 1444015  10/1969  (DE) .

OTHER PUBLICATIONS

Abstract of DE 2335570 Chemical Abstract 80: 146982v 1974.
Abstract of JP 598355—Chemical Abstract 18002, 1957.

* cited by examiner

Primary Examiner—Mukund J. Shah
Assistant Examiner—Venkataraman Balasubramanian
(74) Attorney, Agent, or Firm—Norris McLaughlin & Marcus

(57) ABSTRACT

Process for the preparation of stilbene-disulphonic acids containing bis-alkoxy-triazinyl-amino, or derivatives thereof, characterized in that stilbene-disulphonic acids containing bis-chlorotriazinyl-amino, or derivatives thereof, are reacted with at least 10 molar equivalents, based on the stilbene-disulphonic acid compound, of a $C_1$–$C_4$-monoalkanol.

7 Claims, No Drawings

PROCESS FOR PREPARING BIS-ALKOXY-TRIAZINYL-AMINO-CONTAINING STILBENE DISULPHONIC ACIDS OR THEIR DERIVATIVES

The invention relates to a process for the preparation of stilbene-disulphonic acids containing bis-alkoxy-triazinyl-amino, or derivatives thereof, and to their use as optical brighteners for organic material, chiefly for paper and cellulose, in particular for photographic paper. Optical brighteners based on substituted bis-triazinylamino-stilbene-2,2'-disulphonic acids in which in each case each triazine radical is substituted by an alkoxy radical, in addition to the substitution by the flavonic acid and a further amine, and a process for their preparation are known in large numbers.

The alkoxy radical is usually introduced only in the first or in the second stage in the presence of an acid-binding agent. Thus, an alkanol is reacted with cyanuric chloride or with a cyanuric chloride derivative which still contains two chlorine atoms. Considerable undesirable side reactions due to multiple reactions on the cyanuric chloride occur here. Introduction of an alkoxy group in the third stage, i.e. into a cyanuric chloride derivative which still contains only one chlorine atom, requires special conditions, such as, for example, working in anhydrous glycols or glycol monoalkyl ethers in the presence of the corresponding sodium alcoholate (DE-A 1 444 015).

In JP-A 305 983, bis-triazinylamino-stilbene-2,2'-disulphonic acid derivatives are reacted with methanol in a ratio of 1:2 or with a slight excess of methanol.

DE-A-2 335 570 reports that if glycols or glycol monoalkyl ethers are used, it is possible to react these with bis-triazinylamino-stilbene-2,2'-disulphonic acid derivatives, i.e. with a cyanuric chloride derivative which still carries only one chlorine atom on each triazine ring, in the third stage. However, the yield of this procedure is only between 50 and 80% and therefore makes the process unattractive. There was thus a need for a process with which exactly one $C_1$–$C_4$-alkoxy radical per cyanuric chloride unit can be incorporated selectively and with improved yields into bis-triazinylamino-stilbene-2,2'-disulphonic acids without the use of sophisticated and expensive reagents.

A process has now been found for the preparation of stilbene-disulphonic acids containing bis-alkoxy-triazinyl-amino, or derivatives thereof, in which stilbene-disulphonic acids containing bis-chloro-triazinyl-amino are reacted with a $C_1$–$C_4$-monoalkanol, characterized in that at least 10 mol of $C_1$–$C_4$-monoalkanol are employed per mol of the stilbene-disulphonic acid containing bis-chloro-triazinyl-amino, or derivatives thereof.

In a preferred embodiment, at least 20 mol of the $C_1$–$C_4$-monoalkanol are employed per mol of a stilbene-disulphonic acid containing bis-chloro-triazinyl-amino, or derivatives thereof. Particularly preferably, 50–500 mol, in particular 100–300 mol, of $C_1$–$C_4$-monoalkanol are employed per mol of stilbene-sulphonic acid compound containing bis-chloro-triazinyl-amino.

In an embodiment which is also preferred, the $C_1$–$C_4$-monoalkanol is employed together with water, the water content of the reaction mixture preferably being 10–80% by weight, preferably 25–60% by weight, based on the reaction mixture.

Methanol, ethanol, isopropanol, n-propanol, n-butanol, sec-butanol or tert-butanol, in particular methanol, are employed as preferred $C_1$–$C_4$-monoalkanols. The process for the preparation of 4,4'-bis[6-alkoxy-1,3,5-triazin-2-yl-amino]stilbene-2,2'-disulphonic acid, or derivatives thereof, in which the triazinyl radicals are in each case substituted with amine radicals in the 4-position, is particularly preferred.

The process according to the invention is preferably carried out in the presence of an acid-binding agent, an alkali metal hydroxide, in particular potassium hydroxide or sodium hydroxide, preferably being used as the acid-binding agent. The acid-binding agent is preferably employed in an amount of 2 to 6 molar equivalents per mol of the stilbene-disulphonic acid containing bis-chloro-triazinyl-amino, or derivatives thereof, preferably in an amount of 3 to 4 molar equivalents.

The process according to the invention is as a rule carried out at temperatures from 0C up to the boiling point of the reaction mixture, preferably at 15 to 80° C. In a preferred embodiment of the process according to the invention, compounds of the general formula (I)

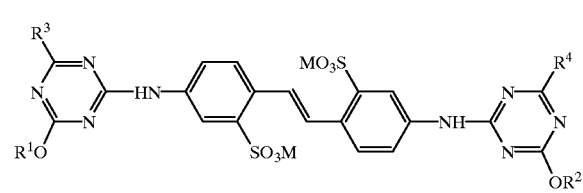

wherein

M represents hydrogen, an alkali metal ion or an optionally substituted ammonium ion, $R^1$ and $R^2$ independently of one another denote $C_1$–$C_4$-alkyl and $R^3$ and $R^4$ independently of one another represent an amine radical, are prepared.

The preferred compounds of the formula (I) prepared by the process according to the invention are obtained by reaction of compounds of the formula (II)

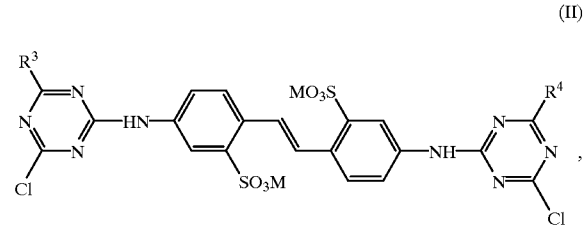

wherein $R^3$, $R^4$ and M have the abovementioned meanings, with $C_1$–$C_4$-monoalkanols.

Compounds of the formula (II) are obtained, for example, by reaction of 2 equivalents of cyanuric chloride with one equivalent of a compound of the formula (III)

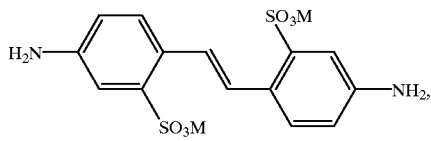

(III)

and a total of 2 equivalents of the compounds R³H and R⁴H in any desired sequence.

The process according to the invention in which the compounds of the formula (II) are not intermediately isolated after their preparation is preferred. It is particularly preferable here to employ the compound of the formula (II) in the preparation process according to the invention in the form of its aqueous reaction solution, if appropriate after concentration and if appropriate (partial) desalination.

In another preferred embodiment of the process according to the invention, the compounds of the formula (I) are obtained starting from a compound of the formula (II)

In a particularly preferred embodiment, the radicals $R^3$, $R^4$ as well as $R^1$ and $R^2$ are identical.

The radical M, which preferably represents hydrogen or an alkali metal, such as sodium, potassium or lithium, does not have to be identical on each sulphonic acid group in the molecule.

It is furthermore preferable to adjust the reaction mixture obtainable by the process according to the invention to a pH of less than 10, preferably less than 8, for the purpose of working up, and to remove the excess $C_1$–$C_4$-monoalkanol, preferably by distillation.

The invention furthermore relates to compounds of the formula (I) which correspond to the formula (IV)

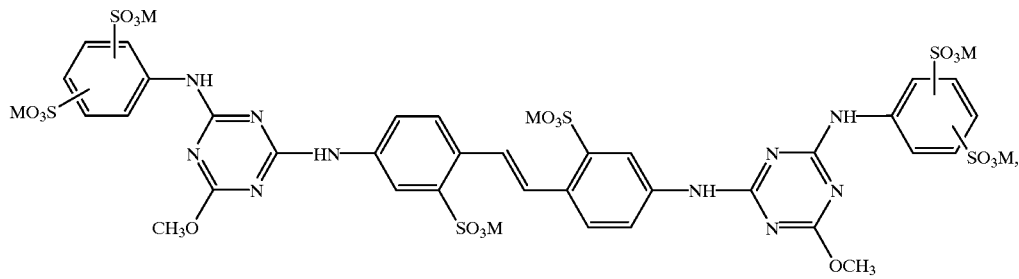

(IV)

wherein $R^3$ and $R^4$ independently of one another represent $NR^5R^6$, wherein $R^5$ represents hydrogen or optionally substituted $C_1$–$C_6$-alkyl and $R^6$ can assume the meanings given under $R^5$ or denotes optionally substituted $C_1$–$C_8$-cycloalkyl or optionally substituted $C_6$–$C_{10}$-aryl, or $NR^5R^6$ represents optionally $C_1$–$C_4$-alkyl-, in particular methyl-substituted, morpholino, piperidino or hexamethylene-imino.

Preferred substituents of the $C_1$–$C_6$-alkyl radical in the meaning of $R^5$ and $R^6$ are, for example, hydroxyl, $C_1$–$C_6$-alkoxy, $C_2$–$C_8$-alkoxy-substituted $C_2$–$C_2$-alkoxy, $C_1$–$C_6$-alkylamino or $C_1$–$C_6$-dialkylamino, cyano or sulphonic acid or sulphonate.

Preferred substituents of the $C_5$–$C_8$-cycloalkyl are: halogen, in particular fluorine, chlorine and bromine, $C_1$–$C_6$-alkyl, $C_1$–$C_6$-alkoxy, sulphamoyl or sulphonyl, in particular $C_1$–$C_4$-alkyl.

Possible optionally substituted $C_6$–$C_{10}$-aryl is, in particular, sulpho-substituted phenyl.

Especially preferably, $R^5$ represents hydrogen, methyl, sulphoethyl or an alkali metal salt thereof or hydroxyethyl, and $R^6$ represents sulphoethyl or an alkali metal salt thereof, hydroxyethyl or disulpho-substituted phenyl.

wherein
M has the abovementioned meaning.

Preferred compounds of the formula (IV) are those in which the $SO_3M$ groups of the terminal benzene ring are in the 2- and 5-position.

The compounds of the formula (IV) can be prepared by a procedure analogous to that described above.

The invention furthermore relates to mixtures comprising at least two different compounds of the formula (I), these being prepared by a procedure analogous to that described above.

Mixtures which comprise three different compounds of the formula (I) in which $R^1$ and $R^2$ represent methyl and $R^3$ and $R^4$ independently of one another represent an amine radical are preferred.

Mixtures comprising at least three different compounds of the formula (I), (Ia) to (Ie), wherein
in (Ia) $R^3=R^4$
in (Ib) $R^3=R^4$ but differs from $R^3$ in (Ia) and
in (Ie) $R^3$ is not the same as $R^4$
are particularly preferred.

Especially preferred mixtures are those of compounds of the formula V, VI and VII

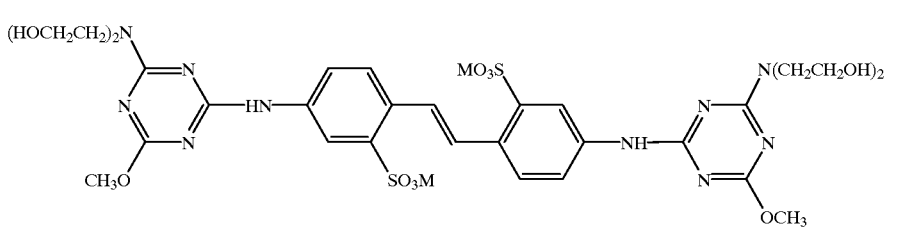
(V)

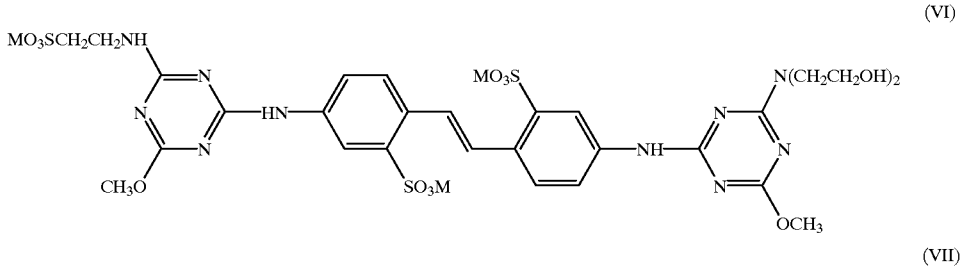
(VI)

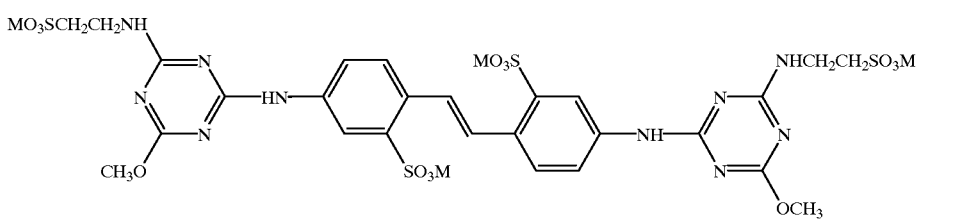
(VII)

wherein
M has the abovementioned meaning.

Mixtures which comprise
10–25% of compound V
25–70% of compound VI and
25–70% of compound VII
are of particular interest.

The compounds (1) prepared by the process according to the invention and the new compounds of the formula (IV) are outstandingly suitable as optical brighteners for organic materials, preferably for cellulose, polyamide, wool, silk and paper, in particular for photographic paper. They can also be added to detergents. The compounds of the formula (I) can, for example, be incorporated in bulk or applied to the surface of the materials to be brightened. Amounts which are particularly preferably employed are 0.0001 to 2% by weight, based on the material to be brightened.

The percentage data stated in the following examples are in each case percentages by weight.

EXAMPLE 1

1,000 g of methanol which comprises 10% of water are initially introduced into the reaction vessel. 185 g of 10% strength sodium hydroxide solution are then added. The temperature is brought to 35° C. A solution, heated to about 35° C., of 167 g of 4,4'-bis[(4-(2,5-disulpho)anilino-6-chloro-1,3,5-triazin-2-yl)amino]-stilbene-2,2'-disulphonic acid hexasodium salt in 1275 ml of water is then added dropwise at 35° C. in the course of 1 hour. The temperature is maintained for 2 hours.

Directly after the reaction, the pH is brought to 6.5 to 7.0 in the course of about 1 hour by addition of 10% strength hydrochloric acid. Thereafter, methanol or methanol/water is distilled off until a constant boiling point of 100° C. is reached. The batch is topped up to 1500 ml with water at about 30° C.

The solution is then filtered with suction, first over a blue band filter and then over a 0.8 μm filter, in order to free the solution from all the sediments and suspended substances which impede the permeate flow. The 1500 ml are introduced into a pressure permeation unit. The first 500 ml of permeate are removed at 40 to 50° C. under about 40 bar. 500 ml of water are added and the second approximately 500 ml of permeate are removed. 500 ml of water are added and the third approximately 500 ml of permeate are removed. 500 ml of water are added and the fourth approximately 500 ml of permeate are removed. The concentrate is evaporated to dryness in a crystallizing dish in a vacuum drying cabinet (50° C.) and the residue is comminuted in a mortar.

Yield: 160 g of yellow powder of 4,4'-bis[(4-(2,5-disulpho)anilino-6-methoxy-1,3,5-triazin-2-yl)amino]-stilbene-2,2'-disulphonic acid hexasodium salt.

The product comprises less than 2% of NaCl and about 1% of $H_2O$, so that a yield of about 94% of theory results.

EXAMPLE 2

1,000 g of methanol which comprises 5% of water are initially introduced into the reaction vessel. 185 g of 10% strength sodium hydroxide solution are then added. The temperature is brought to 40° C. 1,200 ml of an aqueous solution which comprises about 65 g of 4-[(4-diethanolamino-6-chloro-1,3,5-triazin-2-yl)amino]4'-[(4-sulphoethylamino-6-chloro-1,3,5-triazin-2-yl)amino] stilbene-2,2'-disulphonic acid trisodium salt, 15 g of 4,4'-bis[(4-diethanolamino-6-chloro-1,3,5-triazin-2-yl)amino]-stilbene-2,2'-disulphonic acid disodium salt and 65 g of 4,4'-bis[(4-sulphoethylamino-6-chloro-1,3,5-triazin-2-yl) amino]stilbene-2,2'-disulphonic acid tetrasodium salt are then introduced at 40° C. in the course of 1 hour. The temperature is maintained for 2 hours.

Directly after the reaction, the pH is brought to 6.5 to 7.0 in the course of about 1 hour by addition of 10% strength hydrochloric acid. Thereafter, methanol or methanol/water is distilled off until a constant boiling point of 100° C. is reached. The batch is topped up to 1800 ml with water at about 40 to 50° C. The solution is then filtered with suction, first over a blue band filter and then over a 0.8 µm filter, in order to free the solution from all the sediments and suspended substances which impede the permeate flow. The 1800 ml are introduced into a pressure permeation unit. The first 600 ml of permeate are removed at 40 to 50° C. under about 40 bar. 600 ml of water are added and the second approximately 600 ml of permeate are removed. 600 ml of water are added and the third approximately 600 ml of permeate are removed. 600 ml of water are added and the fourth approximately 600 ml of permeate are removed. The concentrate is evaporated to dryness in a crystallizing dish in a vacuum drying cabinet (50° C.) and the residue is comminuted in a mortar.

Yield: 140 g of a pale yellow powder.

The product comprises less than 1% of NaCl and less than 1% of water, so that a yield of 95% of theory results.

EXAMPLE 3

1,000 g of methanol which comprises 5% of water are initially introduced into the reaction vessel. 185 g of 10% strength sodium hydroxide solution are then added. The temperature is brought to 45° C. 600 ml of an aqueous solution, heated to 45° C., which comprises about 65 g of 4-[(4-diethanolamino-6-chloro-1,3,5-triazin-2-yl)amino]4'-[(4-sulphoethylamino-6-chloro-1,3,5-triazin-2-yl)amino]-stilbene-2,2'-disulphonic acid trisodium salt, 15 g of 4,4'-bis[(4-diethanolamino-6-chloro-1,3,5-triazin-2-yl)amino]-stilbene-2,2'-disulphonic acid disodium salt and 65 g of 4,4'-bis[(4-sulphoethylamino-6-chloro-1,3,5-triazin-2-yl)amino]stilbene-2,2'-disulphonic acid tetrasodium salt are then introduced at 45° C. in the course of 1 hour. The temperature is maintained for 2 hours.

Directly after the reaction, the pH is brought to 6.5 to 7.0 in the course of about 1 hour by addition of 10% strength hydrochloric acid. Thereafter, methanol or methanol/water is distilled off until a constant boiling point of 100° C. is reached. The batch is topped up to 1200 ml with water at about 50° C. The solution is then filtered with suction, first over a blue band filter and then over a 0.8 µm filter, in order to free the solution from all the sediments and suspended substances which impede the permeate flow. The 1200 ml are introduced into a pressure permeation unit. The first 400 ml of permeate are removed at about 50° C. under about 40 bar. 400 ml of water are added and the second approximately 400 ml of permeate are removed. 400 ml of water are added and the third approximately 400 ml of permeate are removed. 400 ml of water are added and the fourth approximately 400 ml of permeate are removed. The concentrate is evaporated to dryness in a crystallizing dish in a vacuum drying cabinet (50° C.) and the residue is comminuted in a mortar Yield: 140 g of yellow powder.

The product comprises less than 1% of NaCl and less than 1% of water, so that a yield of 95% of theory results.

EXAMPLE 4

1,000 g of ethanol which comprises 10% of water are initially introduced into the reaction vessel. 185 g of 10% strength sodium hydroxide solution are then added. The temperature is brought to 45° C. A solution, heated to about 45° C., of 167 g of 4,4'-bis[(4-(2,5-disulpho)anilino-6-chloro-1,3,5-triazin-2-yl)amino]-stilbene-2,2'-disulphonic acid hexasodium salt in 1,275 ml of water is then added dropwise at 45° C. in the course of 1 hour. The temperature is maintained for 4 hours.

Directly after the reaction, the pH is brought to 6.5 to 7.0 in the course of about 1 hour by addition of 10% strength hydrochloric acid. Thereafter, ethanol or ethanol/water is distilled off until a constant boiling point of 100° C. is reached. The batch is topped up to 1500 ml with water at about 50° C.

The solution is then filtered with suction, first over a blue band filter and then over a 0.8 µm filter, in order to free the solution from all the sediments and suspended substances which impede the permeate flow. The 1500 ml are introduced into a pressure permeation unit. The first 500 ml of permeate are removed at 40 to 50° C. under about 40 bar. 500 ml of water are added and the second approximately 500 ml of permeate are removed. 500 ml of water are added and the third approximately 500 ml of permeate are removed. 500 ml of water are added and the fourth approximately 500 ml of permeate are removed.

The concentrate is evaporated to dryness in a crystallizing dish in a vacuum drying cabinet (50° C.) and the residue is comminuted in a mortar.

Yield: 165 g of yellow powder of 4,4'-bis[(4-(2,5-disulpho)anilino-6-ethoxy-1,3,5-triazin-2-yl)amino]-stilbene-2,2'-disulphonic acid hexasodium salt.

The product comprises less than 2% of NaCl and less than 2% of water, so that a yield Of 93% of theory results.

EXAMPLE 5

425 g of methanol and 75 ml of water are initially introduced into the reaction vessel. 18 g of 45% strength sodium hydroxide solution are then added. 83 g of 4,4'-bis(2-anilino-6-chloro-1,3,5-triazin-2-yl)amino]-stilbene-2,2'-disulphonic acid disodium salt with a water content of 40% are then introduced. The mixture is heated to the reflux temperature. After 1 hour at the reflux temperature, 10 ml of saturated sodium chloride solution are added at about 70° C., the mixture is allowed to come to room temperature and the solid is filtered off with suction, washed with 160 g of methanol and dried at 50° C. in vacuo.

Yield: 49 g of yellow product of 4,4'-bis(2-anilino-6-methoxy-1,3,5-triazin-2-yl)amino]-stilbene-2,2'-disulphonic acid disodium salt, corresponding to 99.5% of theory.

EXAMPLE 6

800 g of methanol and 350 ml of water are initially introduced into the reaction vessel. 81 g of 10% strength sodium hydroxide solution are then added. 100 g of 4,4'-bis[(2-(4-sulpho)anilino-6-chloro-1,3,5-triazin-2-yl)amino]-stilbene-2,2'-disulphonic acid tetrasodium salt with a water content of 40% are then introduced. The mixture is heated to 60° C. and kept at 60° C. for 1 hour.

Directly thereafter, the pH is brought to 6.5 to 7.0 in the course of about 1 hour by addition of 10% strength hydrochloric acid. Thereafter, methanol or methanol/water is distilled off until a constant boiling point of 100° C. is reached. The batch is topped up to 500 ml with water at about 50° C. and brought to pH 9.0 with 10% strength sodium hydroxide solution.

The solution is then filtered with suction, first over a blue band filter and then over a 0.8 µm filter, in order to free the solution from all the sediments and suspended substances which impede the permeate flow.

The 500 ml are introduced into a pressure permeation unit. The first 150 ml of permeate are removed at 40–50° C. under about 40 bar. 150 ml of water are added and the second approximately 150 ml of permeate are removed. 150 ml of water are added and the third approximately 150 ml of permeate are removed. 150 ml of water are added and the fourth approximately 150 ml of permeate are removed. The concentrate is evaporated to dryness in a crystallizing dish in a vacuum drying cabinet (50° C.) and the residue is comminuted in a mortar.

Yield: 56 g of yellow powder of 4,4'-bis[(2-(4-sulpho)anilino-6-methoxy-1,3,5-triazin-2-yl)amino]-stilbene-2,2'-disulphonic acid tetrasodium salt.

The product still comprises 1% of NaCl and 2% of water, so that a yield of 92% of theory results.

What is claimed is:

1. A process for the preparation of stilbene-disulphonic acids containing bis-alkoxy-triazinyl-amino, wherein a stilbene-disulphonic acid containing bis-chloro-triazinyl-amino, is reacted with a $C_1$–$C_4$-monoalkanol, at least 10 mol of $C_1$–$C_4$-monoalkanol being employed per mol of the stilbene-disulphonic acid containing bis-chloro-triazinyl-amino, whereby the $C_1$–$C_4$-monoalkanol is employed together with water and the water content of the reaction mixture is 10–80% by weight based on the total weight of the reaction mixture.

2. The process according to claim 1, wherein at least 20 mol of $C_{14}$–$C_4$-monoalkanol are employed per mol of the stilbene-sulphonic acid containing bis-chloro-triazinyl-amino.

3. The process according to claim 1, wherein methanol is used as the $C_1$–$C_4$-monoalkanol.

4. The process according to claim 1, wherein the reaction is carried out in the presence of an acid-binding, in particular an alkali metal hydroxide.

5. The process according to claim 1, wherein the stilbene-disulphonic acid containing bis-alkoxy-triazinyl-amino corresponds to the formula (I)

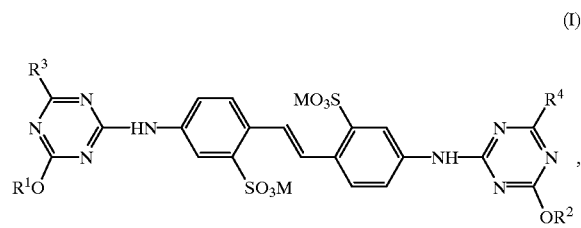

wherein

M represents hydrogen, an alkali metal ion or an ammonium ion, $R^1$ and $R^2$ independently of one another represent $C_1$–$C_4$-alkyl and $R^3$ and $R^4$ independently of one another represent an amine radical, and is prepared starting from compounds of the formula (II)

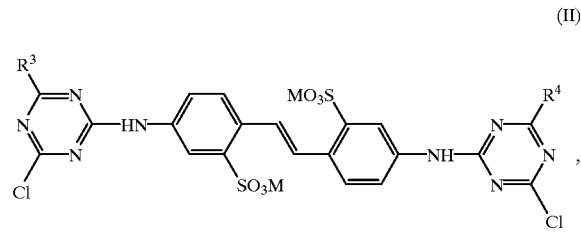

wherein $R^3$, $R^4$ and M have the abovementioned meaning.

6. The process according to claim 1, wherein the water content of the reaction mixture is 25–65% by weight, based on the total weight of the reaction mixture.

7. The process according to claim 1, wherein the reaction is carried out in the presence of an alkali metal hydroxide.

* * * * *

UNITED STATES PATENT AND TRADEMARK OFFICE
CERTIFICATE OF CORRECTION

PATENT NO.    : 6,248,887 B1
DATED         : June 19, 2001
INVENTOR(S)   : Ulrich Feldhues et al.

It is certified that error appears in the above-identified patent and that said Letters Patent is hereby corrected as shown below:

<u>Column 9,</u>
Lines 33 thru 35, change Claim 4 from "The process according to claim 1, wherein the reaction is carried out in the presence of an acid-binding, in particular an alkali metal hydroxide" to -- The process according to claim 1, wherein the reaction is carried out in the presence of an acid binding agent. --

Signed and Sealed this

Ninth Day of September, 2003

JAMES E. ROGAN
*Director of the United States Patent and Trademark Office*